United States Patent [19]

Jasserand et al.

[11] Patent Number: 6,165,985
[45] Date of Patent: Dec. 26, 2000

[54] 11-ACETYL-12,13-DIOXABICYCLO[8.2.1]-TRIDECENONE DERIVATIVES, PROCESSES FOR THEIR PREPARATION AND PHARMACEUTICAL COMPOSITIONS COMPRISING THEM

[75] Inventors: Daniel Jasserand, Hannover; Ulf Preuschoff, Ahlten; Christian Eeckhout, Lindwedel, all of Germany

[73] Assignee: Solvay Pharmaceuticals GmbH, Hannover, Germany

[21] Appl. No.: 09/338,602

[22] Filed: Jun. 23, 1999

Related U.S. Application Data

[63] Continuation-in-part of application No. 09/247,605, Feb. 10, 1999, abandoned.

[30] Foreign Application Priority Data

Feb. 13, 1998 [DE] Germany ............................ 198 05 822

[51] Int. Cl.$^7$ ............................ A61K 31/70; C07H 17/08
[52] U.S. Cl. .............................. 514/28; 514/29; 536/7.1; 536/7.2; 536/18.5
[58] Field of Search ............................ 536/7.1, 7.2, 18.5; 514/28, 29

[56] References Cited

U.S. PATENT DOCUMENTS

| 4,920,102 | 4/1990 | Gidda et al. ............................... 514/28 |
| 5,106,961 | 4/1992 | Kirst ......................................... 536/7.2 |
| 5,418,224 | 5/1995 | Hoeltje et al. ............................ 514/28 |
| 5,712,253 | 1/1998 | Lartey et al. ............................. 514/28 |

FOREIGN PATENT DOCUMENTS 349 100 A2   4/1989   European Pat. Off. .

*Primary Examiner*—Elli Peselev
*Attorney, Agent, or Firm*—Evenson, McKeown, Edwards & Lenahan, P.L.L.C.

[57] ABSTRACT

Ring-contracted N-demethyl-N-isopropyl-erythromycin-A derivatives having a modified side chain and gastrointestinally effective motilin-agonistic properties and the preparation thereof are described.

14 Claims, No Drawings

11-ACETYL-12,13-DIOXABICYCLO[8.2.1]-TRIDECENONE DERIVATIVES, PROCESSES FOR THEIR PREPARATION AND PHARMACEUTICAL COMPOSITIONS COMPRISING THEM

This application is a continuation-in-part of U.S. application Ser. No. 09/247,605 filed on Feb. 10, 1999, now abandoned.

BACKGROUND OF THE INVENTION

The present invention relates to novel N-substituted (2R, 3S,4S,5R,6R,10R,11R)-3-[(2,6-dideoxy-3-C-methyl-3-O-methyl-α-L-ribohexopyranosyl)-oxy]-5-[(3,4,6-trideoxy-3-amino-β-D-xylohexopyranosyl)-oxy]-2,4,6,8,10-pentamethyl-11-acetyl-12,13-dioxabicyclo[8.2.1]-tridec-8-en-1-one compounds with motilin-agonistic properties and to the acid addition salts thereof and also to pharmaceutical formulations containing these compounds and to processes for the preparation of these compounds. The compounds according to the invention are ring-contracted N-demethyl-N-isopropyl derivatives of erythromycin A with a modified side chain.

The antibiotic erythromycin A is known to have, in addition to its antibiotic effects, also gastrointestinal side effects which are undesirable for antibiotics, inter alia a great increase in the contraction activity in the gastrointestinal region with gastric and intestinal cramps, nausea, vomiting and diarrhoea.

There have been several attempts to modify erythromycin A so as to obtain derivatives in which the antibiotic effect is virtually no longer present, but an effect influencing the motility of the gastrointestinal tract is retained. U.S. Pat. No. 5,418,224 (=EP 550,895) discloses ring-contracted N-demethyl-N-isopropyl-erythromycin A derivatives having gastrointestinally effective motilin-agonistic properties.

Furthermore, similar ring-contracted erythromycin derivatives are known from U.S. Pat. No. 5,106,961 (=EP 382,472), but these have antibiotic effects.

SUMMARY OF THE INVENTION

The object of the present invention is to provide novel, orally-effective ring-contracted derivatives of erythromycin A without an antibiotic effect and with properties having a beneficial effect on the motility of the gastrointestinal tract with an improved activity profile.

It has now been found that the novel ring-contracted N-demethyl-N-isopropyl derivatives of erythromycin A, the side chain of which in the 11 position of the cyclic parent structure has been modified by oxidation, are not antibiotically effective, but have selective motilin-agonistic properties and stimulate the motility of the gastrointestinal tract in a beneficial way and show effects enhancing the tone of the lower esophagus sphincter and the tone of the stomach.

Because of their activity profile, the substances according to the invention are suitable for the treatment of motility disturbances in the gastrointestinal tract and moreover are distinguished by good compatibility and good oral effectiveness.

DETAILED DESCRIPTION OF PREFERRED EMBODIMENTS

The present invention therefore relates to novel (2R,3S, 4S,5R,6R,10R,11R)-2,4,6,8,10-pentamethyl-11-acetyl-12, 13-dioxabicyclo [8.2.1]-tridec-8-en-1-one compounds of formula I

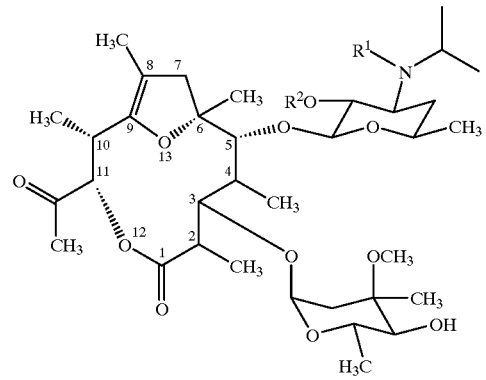

wherein
$R^1$ denotes hydrogen or methyl, and
$R^2$ denotes hydrogen or lower alkanoyl, and the stable acid addition salts and physiologically compatible acid addition salts thereof.

If in compounds of Formula I one substituent is or contains lower alkyl, this may be branched or unbranched, and may have 1 to 4 carbon atoms. The compounds of Formula I in which $R^1$ is methyl have proved particularly beneficial.

$R^2$ preferably represents hydrogen. If $R^2$ is lower alkanoyl, acetyl is preferred.

The compounds of Formula I can be obtained in that, in known manner, in a compound of the general formula II,

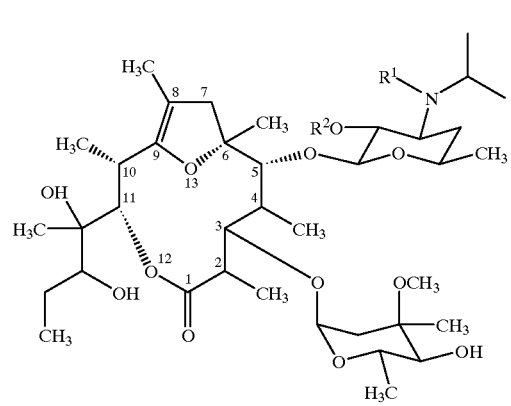

in which $R^1$ and $R^2$ have the above meanings, the 2',3'-dihydroxypent-2'-yl side chain in the 11 position of the cyclic parent structure is converted by oxidative glycol cleavage into an acetyl side chain and, if desired, a methyl group $R^1$ is introduced into the resulting compound of Formula I in which $R^1$ denotes hydrogen, or the methyl group $R^1$ is cleaved off in the resulting compound of Formula I in which $R^1$ denotes methyl, and, if desired, free compounds of Formula I are converted into the stable acid addition salts thereof, or the acid addition salts are converted into the free compounds of Formula I.

The oxidative glycol cleavage of the 2',3'-dihydroxy-pent-2'-yl side chain in the 11 position of the cyclic parent structure of compounds of Formula II can be performed using suitable oxidation agents such as lead tetraacetate in solvents suitable for this purpose. Suitable solvents include non-polar or weakly polar solvents such as benzene, toluene or xylene. The reaction may be performed at temperatures between 0° C. and 40° C., preferably at room temperature.

The resulting compounds of Formula I in which $R^1$ denotes hydrogen can, if desired, subsequently be alkylated in known manner to give the corresponding N-methyl compounds. The alkylation can take place in known manner by reaction with a methyl halide or as reductive alkylation by reaction with formaldehyde under reducing conditions, and can be carried out, for example, in the presence of a reducing agent, for example of a complex borohydride compound such as sodium cyanoborohydride, sodium triacetoxyborohydride or sodium borohydride. If desired, the alkylation can also be carried out by reaction with a methyl halide, especially methyl iodide, or with a methylsulfonic acid ester. The alkylation is advantageously carried out in an organic solvent which is inert under the reaction conditions. Suitable solvents for the reductive alkylation include cyclic ethers such as tetrahydrofuran (=THF) or dioxane, aromatic hydrocarbons such as toluene, or alternatively lower alcohols. The alkylation can be carried out at temperatures between room temperature and the boiling point of the solvent. The alkylation with a methyl derivative, for example a methyl halide such as methyl iodide, is advantageously carried out in the presence of a base such as, for example, an alkali metal carbonate or a tertiary organic amine.

The methyl group $R^1$ can, if desired, subsequently be cleaved off from the compounds of Formula I in which $R^1$ denotes methyl. The demethylation can be effected in known manner by treating the compound with a halogen, in particular iodine and/or bromine, in an inert solvent in the presence of a suitable base. Suitable bases include, for example, alkali metal alcoholates, alkali metal hydroxides and alkali metal salts of weak organic acids.

The compounds of Formula I can be isolated from the reaction mixture and purified in known manner. Acid addition salts can be converted in conventional manner into the free bases, and the free bases can, if desired, be converted in known manner into pharmacologically compatible acid addition salts. To avoid secondary hydrolysis reactions, it is advantageous to use only equivalent amounts of acids for the salt formation.

Examples of suitable pharmacologically acceptable acid addition salts of the compounds of Formula I include the salts thereof with inorganic acids, for example carbonic acid, hydrohalic acids, especially hydrochloric acid, or with organic acids, for example lower aliphatic mono- or dicarboxylic acids such as maleic acid, fumaric acid, lactic acid, tartaric acid or acetic acid.

The starting compounds of Formula II in which $R^2$ is hydrogen are known from U.S. Pat. No. 5,418,224, the disclosure of which is incorporated herein by reference, and can be prepared according to the processes described therein.

The starting compounds of Formula II in which $R^2$ is lower alkanoyl can be prepared by reacting compounds of Formula II in which $R^2$ is hydrogen with carboxylic acids of the general formula III,

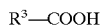

$$R^3\text{—COOH} \qquad \qquad \text{III}$$

in which $R^3$ is lower alkyl, or reactive derivatives of these acids, in known manner.

Suitable reactive derivatives of acids of Formula III include, in particular, optionally mixed acid anhydrides and acid halides. For example, acid chlorides or acid bromides of the acids of Formula III or mixed esters of the acids of Formula III with organic sulfonic acids, for example with lower alkane sulfonic acids optionally substituted by halogen, such as methanesulfonic acid or trifluoromethanesulfonic acid, or with aromatic sulfonic acids such as benzenesulfonic acids or with benzenesulfonic acids substituted by lower alkyl or halogen, e.g. toluenesulfonic acids or bromobenzene-sulfonic acids, can be used. The reaction may be performed as an acylation in an organic solvent which is inert under the reaction conditions at temperatures between −20° C. and room temperature. Suitable solvents include di-lower alkyl ketones, for example acetone, halogenated hydrocarbons such as dichloromethane or aromatic hydrocarbons such as benzene or toluene or cyclic ethers such as THF or dioxane, or mixtures of these solvents.

The acylation can advantageously be carried out in the presence of an acid-binding reagent, particularly if an anhydride or a mixed anhydride of the acids of Formula III with a sulfonic acid is used as acylation agent. Suitable acid-binding reagents include inorganic bases such as alkali metal carbonates, for example potassium carbonate, or organic bases soluble in the reaction mixture, such as tertiary nitrogen bases, for example tert. lower alkylamines and pyridines, such as triethylamine, tripropylamine, N-methylmorpholine, pyridine, 4-dimethylaminopyridine, 4-diethylaminopyridine or 4-pyrrolidinopyridine.

If desired, a methyl group $R^1$ may be introduced into a resulting compound of Formula II in which $R^1$ is hydrogen, or the methyl group $R^1$ in a resulting compound of Formula II in which $R^1$ is methyl can be cleaved off. Such methylation or demethylation operations may be performed in known manner, for example under the conditions described for the introduction or cleavage of a methyl group in the compounds of Formula I.

The novel compounds of Formula I and the physiologically compatible acid addition salts thereof have interesting pharmacological properties, especially motilin-agonistic properties stimulating the motility of the gastrointestinal tract. In this case, they are distinguished by a beneficial activity profile with surprisingly good oral effectiveness. They are free of antibiotic effects and have a high selective affinity for motilin receptors, whereas in dose ranges with motilin-agonistic effectiveness they show no practically relevant affinity for other receptors in the gastrointestinal tract such as adrenaline, acetylcholine, histamine, dopamine or serotonin receptors. The compounds have surprisingly good liver compatibility, which makes them suitable for applications over relatively long periods.

In the healthy state, the autonomic nervous system and hormones in the gastrointestinal tract cooperate to ensure controlled digestion of food consumed and in order to generate a controlled contraction activity of the gastrointestinal tract not only immediately after intake of food but also when the gastrointestinal tract is empty. Motilin is a known gastrointestinal peptide hormone which stimulates the motility of the gastrointestinal tract and induces a coordinated motility throughout the gastrointestinal tract in the fasting state and after intake of food.

The compounds of Formula I show motilin-like physiological effects in that they act as agonists for motilin receptors. Thus, the compounds of Formula I show pronounced stimulating effects in the gastrointestinal region and at the lower esophagus sphincter. In particular, they bring about an increased rate of gastric emptying, an increase in the stomach tone and a long-lasting increase in the resting tone of the esophagus sphincter. Because of their motilin-like activity profile, the substances are suitable for the treatment of conditions which are associated with motility disturbances in the gastrointestinal tract and/or reflux of chyme from the stomach into the esophagus. Thus, the compounds of Formula I are indicated, for example, for gastroparesis with a wide variety of causes, disturbances of the stomach tone, disturbances of gastric emptying and gastro-esophageal reflux, dyspepsia and postoperative disturbances.

The gastrointestinally effective properties of the compounds of Formula I can be demonstrated in standard pharmacological test methods in vitro and in vivo.

DESCRIPTION OF THE TEST METHODS

1. Determination of the binding capacity of the test substances to motilin receptors.

The affinity of the compounds of Formula I for motilin receptors is measured in vitro on a fraction of a tissue homogenate from rabbit antrum. The displacement of radioactively labelled iodinated motilin from motilin receptor binding by the test substances is determined.

The receptor binding studies are carried out by a modification of the process of Borman et al. (Regulatory Peptides 15:143–153 (1986). To prepare the $^{125}$iodine-labelled motilin, motilin is iodinated enzymatically using lactoperoxidase in known manner, for example in analogy to the method described by Bloom et al. (Scand. J. Gastroenterol. 11:47–52 (1976).

To obtain the fraction of tissue homogenate used in the test from rabbit antrum, the antrum from which the mucosa have been removed is comminuted and homogenised in 10 times the volume of a cold homogenisation buffer solution (50 mM tris-HCl buffer, 250 mM sucrose, 25 mM KCl, 10 mM $MgCl_2$, pH 7.4) with the addition of inhibitors (1 mM iodoacetamide, 1 μM pepstatin, 0.1 mM methylsulfonyl fluoride, 0.1 g/l trypsin inhibitor, 0.25 g/l bacitracin) with a homogenizer at 1500 revolutions per minute for 15 sec. The homogenizate is then centrifuged at 1000 g for 15 minutes, the resulting residue is washed four times with homogenization buffer solution and finally re-suspended in 0.9% strength sodium chloride solution (in a volume corresponding to 5 times the amount by weight of the antrum). The tissue fraction obtained in this way, which is referred to as "crude membrane preparation", is used for the test.

For the binding test, 200 μl of the crude membrane fraction (0.5–1 mg of protein) in 400 μl of a buffer solution A (50 mM tris-HCl buffer, 1.5% bovine serum albumen (BSA), 10 mM $MgCl_2$, pH 8.0) are incubated with 100 μl of iodinated motilin diluted in buffer solution B (10 mM tris-HCl buffer, 1% BSA, pH 8) (final concentration 50 pM) at 30° C. for 60 min. The reaction is stopped by adding 3.2 ml of cold buffer solution B, and bound and non-bound motilin are separated from one another by centrifugation (1000 g, 15 minutes). The residue obtained as pellets after the centrifugation is washed with buffer solution B and counted in a gamma counter. The displacement studies are carried out by adding increasing amounts of the substance to be tested to the incubation medium. The test substance solutions employed are aqueous solutions which are prepared by suitable dilution of 60×10$^{-4}$ molar aqueous stock solutions. Test substances which are sparingly soluble in water are initially dissolved in 60% strength ethanol, and this solution is diluted with sufficient water for the ethanol concentration in the solution to be tested not to exceed 1.6% by volume. The $IC_{50}$ of the particular test substance is determined from the resulting measured data as that concentration which brings about 50% inhibition of the specific binding of the iodinated motilin to the motilin receptors. From this the corresponding $pIC_{50}$ value is calculated. The $pIC_{50}$ values given in Table 1 below were determined for the substances of Examples 1 and 2 using the above method. The Example numbers quoted relate to the preparation examples described below.

TABLE 1

| Example No. | $pIC_{50}$ |
|---|---|
| 1 | 8.01 |
| 2 | 7.75 |

2. In vivo determination of the effect of the substances on the stomach tone.

The stomach tone plays an important role in gastric emptying. An increased stomach tone contributes to an increased rate of gastric emptying.

The influence of substances on the stomach tone is determined on beagles with the aid of a barostat which is connected to a plastic pouch in the stomach of the dog and permits measurement of volume or pressure in the stomach of the dog. With the barostat, the stomach volume is determined at a constant pressure in the stomach or the stomach pressure is determined at a constant volume in the stomach. When the stomach tone increases, a reduced stomach volume is detected at a given pressure, and an increased pressure at a given volume. In the test model used to investigate the increase in stomach tone effected by the substances, the change in stomach volume caused by the substances is measured at constant pressure. The stomach of the test animals is relaxed by intake of lipids, i.e. the stomach tone decreases, which causes the stomach volume to increase correspondingly. The reduction in % of the stomach volume which has been increased by administration of lipids which occurs after intake of the substance due to a re-increase in stomach tone is measured as a measurement of the stomach tone-increasing effect of the substances.

The substance of Example 1 in this test model, administered i.d. in the readily compatible dose of 2.15 μmole/kg, showed a reduction in the stomach volume increased after lipid administration by 59.5%. Oral administration of the above test substance in the same dose of 2.15 μmole/kg caused an unusually marked reduction in the stomach volume, the lipid-induced relaxation of the stomach volume being practically completely hindered. These findings can be used as clear indications of a particularly high, in particular high oral, bioavailability of the substances according to the invention.

3. In vivo determination of the effect of the substances on the resting tone of the lower esophagus sphincter.

This determination is carried out on male, conscious, fasting beagles which, before the start of the test, have each been provided with an esophagus fistula and a duodenal cannula. The pressure of the lower esophagus sphincter is measured by means of a perfused catheter system which has a lateral opening and which is connected to a pressure transducer and a recorder. The catheter is passed through the esophagus fistula into the stomach and then slowly withdrawn manually (=pull-through manometry). A peak is recorded when the catheter part with the lateral opening passes through the high-pressure zone of the lower esophagus sphincter. The pressure in mm Hg is determined from this peak.

In this way, initially the basal pressure of the esophagus sphincter is determined as control value. Subsequently, the test substance is administered orally and, after 15 min., the pressure at the lower esophagus sphincter is measured at 2-minute intervals for a period of 60 min. The increase in the pressure after administration of test substance compared with the previously determined basal pressure is calculated.

In this test, the basal tone of the esophagus sphincter was increased by 143% by oral administration of a dose of 0.464 μmole/kg of the substance of Example 1. This effect persisted throughout the entire 60 min. duration of the test.

Because of their effects in the gastrointestinal tract, the compounds of Formula I are suitable in gastroenterology as medicaments for larger mammals, especially humans, for the prophylaxis and treatment of motility disturbances in the gastrointestinal tract.

The doses to be used may differ between individuals and will naturally vary depending on the nature of the condition to be treated and the form of administration. For example, parenteral formulations will generally contain less active substance than oral preparations. However, in general medicament forms with an active substance content of 1 to 100 mg per single dose are suitable for administration to larger mammals, especially humans.

As medicinal agents, the compounds of Formula I may be contained with conventional pharmaceutical auxiliary substances in pharmaceutical formulations such as, for example, tablets, capsules, suppositories or solutions. These pharmaceutical formulations may be prepared by known methods using conventional solid vehicles such as, for example, lactose, starch or talcum, or liquid diluents such as, for example, water, fatty oils or liquid paraffins, and using customary pharmaceutical auxiliary substances, for example tablet disintegrants, solubilizing agents or preservatives.

The following examples are intended to illustrate the invention in greater detail without restricting its scope in any way.

EXAMPLE 1

(2R,3S,4S,5R,6R,10R,11R]-3-[(2,6-dideoxy-3-C-methyl-3-O-methyl-α-L-ribohexopyranosyl)-oxy]-5-[(3,4,6-trideoxy-3-(N-methyl-N-isopropylamino)-β-D-xylo-hexopyranosyl) -oxy]-2,4,6,8,10-pentamethyl-11-acetyl-12,13-dioxabicyclo[8.2.1]-tridec-8-en-1-one (compound of Formula I, $R^1$=methyl, $R^2$=hydrogen)

A) 100 g [2R(2'R,3'R),3S,4S,5R,6R,10R,11R]-11-(2',3'-dihydroxypent-2'-yl)-3-[(2,6-dideoxy-3-C-methyl-3-O-methyl-α-L-ribohexopyranosyl)-oxy]-5-[(3,4,6-trideoxy-3-(N-methyl-N-isopropylamino)-β-D-xylohexopyranosyl)-oxy]-2,4,6,8,10-pentamethyl-12,13-dioxabicyclo[8.2.1]-tridec-8-en-1-one (=compound of Formula II, $R^1$=methyl, $R^2$=hydrogen) was dissolved in 2500 ml toluene under a nitrogen atmosphere. 100.0 g lead tetraacetate was added to this receiving mixture, and the resulting suspension was stirred for 5 hours at room temperature. Then the reaction mixture was washed successively with saturated sodium hydrogen carbonate solution and then with water until the washing water reacted neutrally. The organic phase was dried over sodium sulfate and evaporated at reduced pressure. Chromatography of the remaining residue on silica gel (mobile solvent: methyl tert. butyl ether=MTBE) yielded 81.9 g of the title compound as a white powder, melting point=198°–200° C., optical rotation $[\alpha]_D^{20}$=24.6° (c=1.0 in $CH_2Cl_2$).

B) 1.1 g of the compound obtained above was dissolved in 1 ml acetonitrile. 0.17 g of malonic acid was added to this receiving mixture, and the mixture was heated to 60°–70° C. Once the solid constituents had dissolved, 10 ml MTBE was added and the mixture was heated to boiling for 5 minutes with reflux cooling. Then another 10 ml MTBE was added, and the mixture was cooled to room temperature with stirring. The resulting crystals were filtered out from the solution, washed twice with 10 ml MTBE each time, and were dried at 60° C. in a vacuum. 1.2 g of the monomalonate of the title compound were obtained, melting range: 115.6–174.6° C. (indefinite).

EXAMPLE 2

(2R,3S,4S,5R,6R,10R,11R)-3-[(2,6-dideoxy-3-C-methyl-3-O-methyl-α-L-ribohexopyranosyl)-oxy]-5-[(3,4,6-trideoxy-2-O-acetyl-3-(N-methyl-N-isopropylamino)-β-D-xylo-hexopyranosyl)-oxy]-2,4,6,8,10-pentamethyl-11-acetyl-12,13-dioxabicyclo[8.2.1]-tridec-8-en-1-one (compound of Formula I, $R^1$=methyl, $R^2$=acetyl)

A) 210.0 g of the starting compound of Example 1 (=compound of Formula II, $R^1$=methyl, $R^2$=hydrogen) was dissolved in 2.4 liters acetone under a nitrogen atmosphere, and 85.8 g potassium carbonate was added thereto. 63.4 g of acetic anhydride was added to this receiving mixture, and the resulting suspension was stirred for 20 hours at room temperature. Then the reaction mixture was poured onto a mixture of 2,400 g ice and 1,000 ml water and was stirred for 30 minutes. The aqueous phase was extracted three times with ethyl acetate, the organic phases were combined, and the excess solvent was evaporated in a vacuum. Recrystallisation of the resulting crude product from n-pentane yielded 200 g [2R(2'R,3'R),3S,4S,5R,6R,10R,11R]-11-(2',3'-dihydroxy-pent-2'-yl)-3-[(2,6-dideoxy-3-C-methyl-3-O-methyl-α-L-ribohexopyranosyl)-oxy]-5-[(3,4,6-trideoxy-2-O-acetyl-3-(N-methyl-N-isopropylamino)-β-D-xylohexopyranosyl)-oxy]-2,4,6,8,10-pentamethyl-12,13-dioxabicyclo[8.2.1]-tridec-8-en-1-one (=compound of Formula II, $R^1$=methyl, $R^2$=acetyl), melting point= 128°–130° C.

B) 10.1 g of the product obtained above were reacted with 9.1 g of lead tetraacetate in the manner described in Example 1. 6.0 g of the title compound was obtained as a white solid, melting point=164° C., optical rotation $[\alpha]_D^{20}$=−23.2° (c=1.0 in $CH_2Cl_2$).

EXAMPLE I

Capsules containing (2R,3S,4S,5R,6R,10R,11R)-3-[(2,6-dideoxy-3-C-methyl-3-O-methyl-α-L-ribohexopyranosyl)-oxy]-5-[(3,4,6-trideoxy-3-(N-methyl-N-isopropylamino)-β-D-xylohexopyranosyl)-oxy]-2,4,6,8,10-pentamethyl-11-acetyl-12,13-dioxabicyclo[8.2.1]-tridec-8-en-1-one:

Capsules containing the active substance were produced using the following auxiliary substances and ingredients per capsule:

| | |
|---|---|
| (2R,3S,4S,5R,6R,10R,11R)-3-[(2,6-dideoxy-3-C-methyl-3-O-methyl-α-L-ribohexopyranosyl)-oxy]-5-[(3,4,6-trideoxy-3-(N-methyl-N-isopropylamino)-β-D-xylohexopyranosyl)-oxy]-2,4,6,8,10-pentamethyl-11-acetyl-12,13-dioxabicyclo[8.2.1]-tridec-8-en-1-one | 20 mg |
| Corn starch | 60 mg |
| Lactose | 301 mg |
| Ethyl acetate (= EA) | q.s. |

The active substance, the corn starch and the lactose were processed to form a homogenous, pasty mixture using ethyl acetate. The paste was comminuted, and the resulting granules were placed on a suitable metal sheet and dried at 45° C. to remove the solvent. The dried granules were passed through a comminuting machine and mixed with the following additional auxiliary substances in a mixer:

| | |
|---|---|
| Talc | 5 mg |
| Magnesium stearate | 5 mg |
| Corn starch | 9 mg | and then poured into 400 mg-capacity capsules (=capsule size 0).

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A (2R,3S,4S,5R,6R,10R,11R)-2,4,6,8,10-pentamethyl-11-acetyl-12,13-dioxabicyclo[8.2.1]-tridec-8-en-1-one compound corresponding to the formula I:

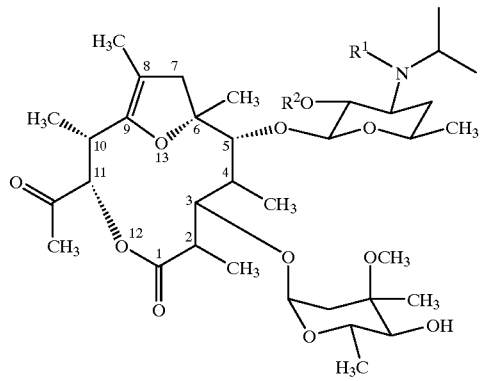

wherein

R$^1$ denotes hydrogen or methyl, and

R$^2$ denotes hydrogen or lower alkanoyl, or a physiologically compatible acid addition salt thereof.

2. A compound according to claim 1, wherein R$^1$ is methyl.

3. A compound according to claim 1, wherein R$^2$ is hydrogen.

4. A pharmaceutical composition comprising a pharmacologically effective amount of a compound according to claim 1, and at least one pharmaceutical carrier or adjuvant.

5. A process for preparing a (2R,3S,4S,5R,6R,10R11R)-2,4,6,8,10-pentamethyl-11-acetyl-12,13-dioxabicyclo[8.2.1]-tridec-8-en-1-one compound corresponding to formula I:

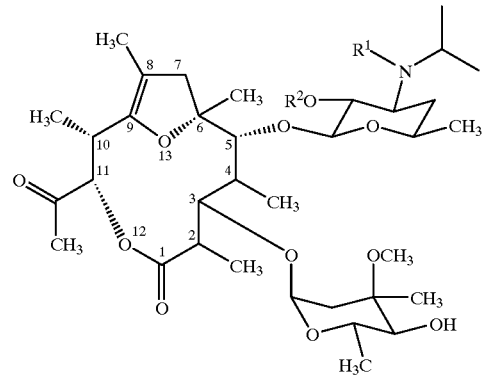

wherein

R$^1$ denotes hydrogen or methyl, and

R$^2$ denotes hydrogen or lower alkanoyl, or a physiologically compatible acid addition salt thereof, said process comprising the steps of:

reacting a compound of formula II

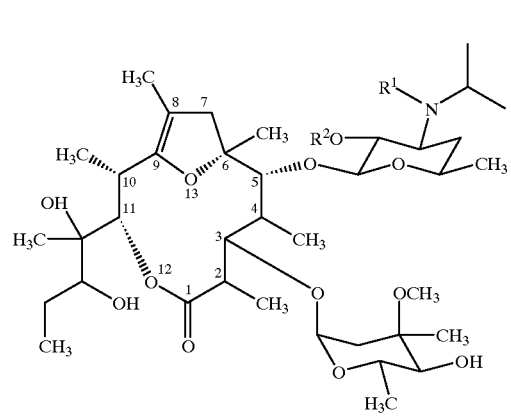

in which R$^1$ and R$^2$ have the above meanings, to convert the 2',3'-dihydroxypent-2'-yl side chain in the 11 position of formula II by oxidative glycol cleavage into an acetyl side chain.

6. A process according to claim 5, wherein R$^1$ in the compound of formula I or formula II denotes hydrogen, further comprising the step of alkylating the compound to obtain a compound in which R$^1$ denotes methyl.

7. A process according to claim 5, wherein R$^1$ in the compound of formula I or formula II denotes methyl, further comprising the step of cleaving of the methyl group to obtain a compound in which R$^1$ denotes hydrogen.

8. A process according to claim 5, wherein the compound of formula I is an acid addition salt, further comprising the step of converting the acid addition salt into a free base.

9. A process according to claim 8, further comprising the step of converting the free base into a stable acid addition salt of a pharmacologically compatible acid.

10. A process for stimulating the gastrointestinal tract of a mammal comprising administering a stomach tone increasing amount of the compound of claim 1, thereby accelerating gastric emptying.

11. A process according to claim 10, wherein said administering is by oral administration.

12. A process for treating gastrointestinal disturbances of a mammal, comprising administering an amount of the compound of claim 1 sufficient to increase a resting tone of the lower esophagus sphincter.

13. A process according to claim 12, wherein said administering is by oral administration.

14. A process according to claim 5, wherein the compound of formula I is a free base, further comprising the step of converting the free base into a stable acid addition salt of a pharmacologically compatible acid.

\* \* \* \* \*